US00PP13237P2

(12) United States Plant Patent
van Leeuwen

(10) Patent No.: US PP13,237 P2
(45) Date of Patent: Nov. 19, 2002

(54) CARNATION PLANT NAMED 'WESDIWIT'

(75) Inventor: Gijsbertus van Leeuwen, 's-Gravenzande (NL)

(73) Assignee: West Select B.V., 's - Gravezande (NL)

( * ) Notice: Subject to any disclaimer, the term of this patent is extended or adjusted under 35 U.S.C. 154(b) by 0 days.

(21) Appl. No.: 10/094,284

(22) Filed: Mar. 8, 2002

(51) Int. Cl.[7] ..... A01H 5/00
(52) U.S. Cl. ..... Plt./279
(58) Field of Search ..... Plt./279

(56) References Cited

U.S. PATENT DOCUMENTS

PP2,480 P * 2/1965 Mittleider ..... Plt./279

OTHER PUBLICATIONS

UPOV–ROM GTITM computer database, GTI JOUVE retrieval software 2002/02, citation for Wesdiwit.*

* cited by examiner

*Primary Examiner*—Bruce R. Campell
*Assistant Examiner*—W C Baker
(74) *Attorney, Agent, or Firm*—C. A. Whealy

(57) ABSTRACT

A distinct cultivar of Carnation plant named 'Wesdiwit', characterized by its compact, upright and rounded plant habit; freely basal branching habit; strong lateral branches; dark green-colored foliage; continuous flowering habit; and white-colored flowers.

1 Drawing Sheet

BOTANICAL CLASSIFICATION/CULTIVAR DESIGNATION

*Dianthus caryophyllus* cultivar Wesdiwit.

BACKGROUND OF THE INVENTION

The present invention relates to a new and distinct cultivar of potted Carnation plant, botanically known as *Dianthus caryophyllus* and hereinafter referred to by the name 'Wesdiwit'.

The new cultivar is a product of a planned breeding program conducted by the Inventor in 's-Gravenzande, The Netherlands. The objective of the breeding program is to create new potted Carnation cultivars having compact plant habit, continuous flowering, and attractive flower coloration.

The new Carnation originated from a cross-pollination made by the Inventor in 's-Gravenzande, The Netherlands, of two unidentified proprietary seedling selections of *Dianthus caryophyllus*, not patented. The new Carnation was discovered and selected by the Inventor as a single flowering plant within the progeny of the stated cross-pollination grown in a controlled environment in 's-Gravenzande, The Netherlands in May, 1999. The selection of this plant was based on its compact plant habit and attractive flower coloration.

Asexual reproduction of the new Carnation by cuttings propagated in a controlled environment in 's-Gravenzande, The Netherlands, since the summer of 1999, has shown that the unique features of this new Carnation are stable and reproduced true to type in successive generations.

SUMMARY OF THE INVENTION

The cultivar Wesdiwit has not been observed under all possible environmental conditions. The phenotype may vary somewhat with variations in environment such as temperature and light intensity without, however, any variance in genotype.

The following traits have been repeatedly observed and are determined to be the unique characteristics of 'Wesdiwit'. These characteristics in combination distinguish 'Wesdiwit' as a new and distinct cultivar:

1. Compact, upright and rounded plant habit.
2. Freely basal branching habit.
3. Strong lateral branches.
4. Dark green-colored foliage.
5. Continuous flowering habit during the flowering season.
6. White-colored flowers.

Compared to plants of the female parent, plants of the new Carnation are more compact, more vigorous and have stronger lateral branches. Compared to plants of the male parent, plants of the new Carnation are more vigorous and differ in flower color.

Plants of the new Carnation can be compared to plants of the cultivar Diogenes, not patented. In side-by-side comparisons conducted in 's-Gravenzande, The Netherlands, plants of the new Carnation and the cultivar Diogenes differed in the following characteristics:

1. Plants of the new Carnation were more compact than plants of the cultivar Diogenes.
2. Flowers of plants of the new Carnation were white in color whereas flowers of plants of the cultivar Diogenes were pink in color.

BRIEF DESCRIPTION OF THE PHOTOGRAPHS

The accompanying colored photographs illustrate the overall appearance of the new Carnation, showing the colors as true as it is reasonably possible to obtain in colored reproductions of this type. Colors in the photographs may differ slightly from the color values cited in the detailed botanical description which accurately describe the colors of the new Carnation.

The photograph at the top of the sheet comprises a side perspective view of a typical flowering plant of 'Wesdiwit' grown in a container.

The photograph at the bottom of the sheet comprises a close-up view of flowers and leaves of a typical plant of 'Wesdiwit'.

DETAILED BOTANICAL DESCRIPTION

In the following description, color references are made to The Royal Horticultural Society Colour Chart, 1995 edition, except where general terms of ordinary dictionary significance are used. The aforementioned photographs, following observations and measurements describe plants grown in 's-Gravenzande, The Netherlands during the summer in a glass-covered greenhouse. During the production of the plants, day temperatures ranged from 20 to 25° C. and night temperatures ranged from 18 to 20° C. Rooted young plants were planted in 10-cm containers and pinched once. The photographs and the description were taken about five months after planting.

Botanical classification: *Dianthus caryophyllus* cultivar Wesdiwit.

Parentage:

*Female, or seed, parent.*—Unidentified proprietary seedling selection of *Dianthus caryophyllus*, not patented.

*Male, or pollen, parent.*—Unidentified proprietary seedling selection of *Dianthus caryophyllus*, not patented.

Propagation:

*Type.*—By cuttings.

*Time to initiate roots.*—About 21 days at 20° C.

*Root description.*—Fine, fibrous.

Plant description:

*Plant habit.*—Compact, upright and rounded.

*Growth habit.*—Freely basal branching; when pinched, potentially 35 lateral branches develop. Moderately vigorous.

*Plant height.*—About 15 cm.

*Plant width.*—About 21.5 cm.

*Lateral branch description.*—Length: About 7.5 cm. Diameter: About 2 mm. Internode length: About 1.75 mm. Aspect: Upright. Strength: Strong. Texture: Glabrous; smooth. Color: 137B.

*Foliage description.*—Arrangement: Leaves simple; symmetrical; abundant; opposite; sessile and decurrent. Length: About 3.5 cm. Width: About 3.5 mm. Shape: Ligulate. Apex: Acute. Margin: Entire. Texture, upper and lower surfaces: Glabrous; smooth. Venation pattern: Parallel, linear. Color: Young foliage, upper and lower surfaces: 144B. Fully expanded foliage, upper surface: 147A. Fully expanded foliage, lower surface: 137A. Venation, upper and lower surfaces: 137C.

Flowering description:

*Appearance.*—Rounded flowers that face upright. One flower per lateral branch; freely flowering, potentially about 35 flowers per plant.

*Flowering response.*—Plants flower during the summer in The Netherlands; during this period, flowering is continuous.

*Postproduction longevity.*—Flowers last about 7 days on the plant. Flowers persistent.

*Fragrance.*—None detected.

*Flower size.*—Diameter: About 4.25 cm. Depth (height): About 2.25 cm.

*Flower buds.*—Length: About 1.75 cm. Diameter: About 8.5 mm. Shape: Ovoid. Color: 146A.

*Petals.*—Quantity/arrangement: About 20 to 25 per flower; rosulate. Length: About 3 cm. Width: About 1.4 cm. Shape: Flabellate. Apex: Rounded, praemorse. Base: Attentuate. Margin: Praemorse. Texture, upper and lower surfaces: Glabrous; satiny. Color: When opening and fully opened, upper surface: Closest to 155D. When opening and fully opened, lower surface: Closest to 155D.

*Sepals.*—Quantity/arrangement: Five per flower fused into a calyx tube. Length: About 1.7 cm. Width: About 5 mm. Shape: Elliptic. Apex: Acute. Texture, upper and lower surfaces: Smooth, leathery; glabrous. Color: Upper surface: 137B. Lower surface: 148C.

*Peduncles.*—Length: About 1.5 cm. Diameter: About 1.5 mm. Aspect: Upright. Strength: Strong. Texture: Smooth; glabrous. Color: 137B.

*Reproductive organs.*—Androecium: Stamen number: About four. Filament length: About 8 mm. Filament diameter: Less than 1 mm. Filament color: 155D. Anther length: Less than 1 mm. Anther shape: Roughly oblong. Anther color: Close to 155D. Pollen: None observed. Gynoecium: Pistil quantity: One. Style length: About 2.3 cm. Style diameter: Less than 1 mm. Style color: 155D. Ovary color: Towards the apex, 144B; towards the base, 145C.

*Seed/fruit.*—Seed and fruit production has not been observed.

Disease/pest resistance: Plants of the new Carnation have not been observed to be resistant to pathogens nor pests common to Carnation.

It is claimed:

1. A new and distinct cultivar of Carnation plant named 'Wesdiwit', as illustrated and described.

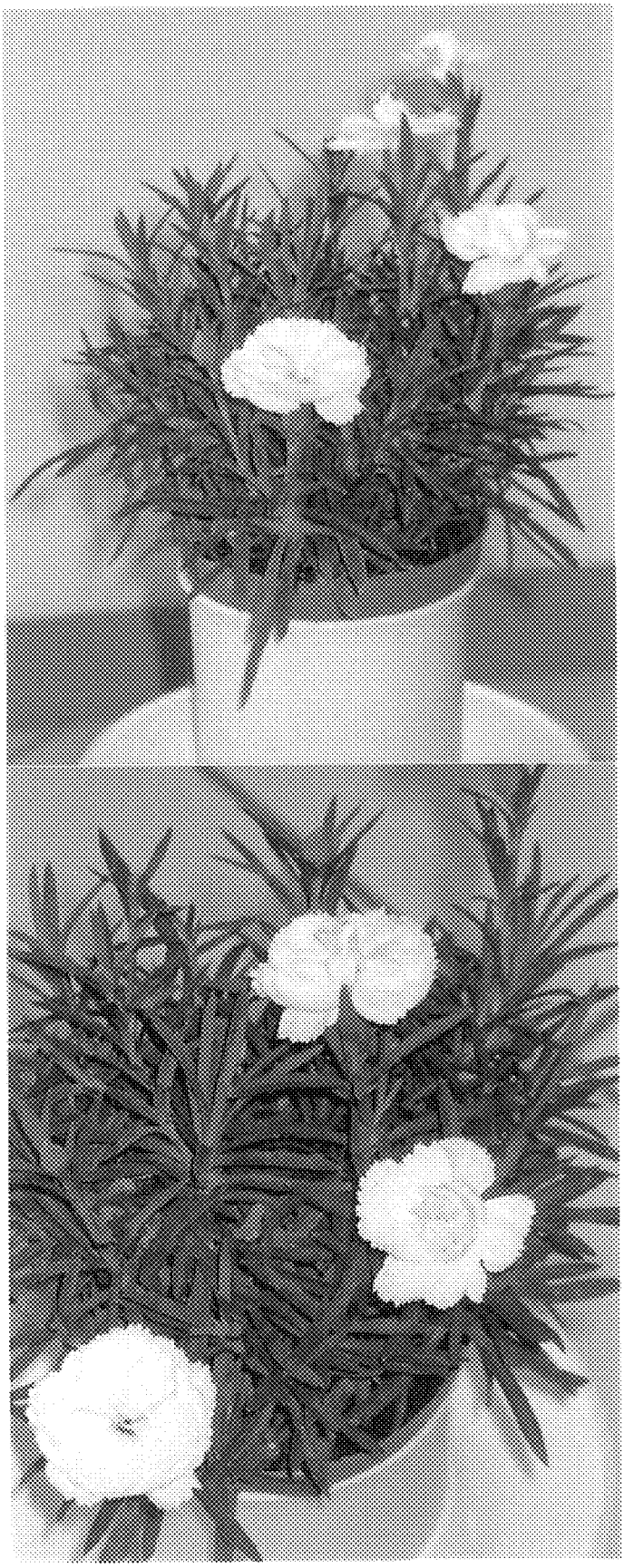

* * * * *